(12) United States Patent
Minosh et al.

(10) Patent No.: US 11,382,785 B2
(45) Date of Patent: Jul. 12, 2022

(54) THERAPEUTIC VESSEL, RELATED FOOTWEAR, AND METHOD OF MANUFACTURE AND USE

(71) Applicants: Joyce Minosh, Westford, MA (US); Adam Rizika, Chestnut Hill, MA (US)

(72) Inventors: Joyce Minosh, Westford, MA (US); Adam Rizika, Chestnut Hill, MA (US)

( * ) Notice: Subject to any disclaimer, the term of this patent is extended or adjusted under 35 U.S.C. 154(b) by 96 days.

(21) Appl. No.: 16/511,598

(22) Filed: Jul. 15, 2019

(65) Prior Publication Data
US 2021/0015649 A1 Jan. 21, 2021

(51) Int. Cl.
*A61F 5/34* (2006.01)
*A61F 5/01* (2006.01)
*A41B 11/00* (2006.01)

(52) U.S. Cl.
CPC .......... *A61F 5/0195* (2013.01); *A41B 11/00* (2013.01); *A61F 5/34* (2013.01); *A41B 2400/322* (2013.01); *A41B 2500/10* (2013.01)

(58) Field of Classification Search
CPC ...... A61F 13/063; A61F 5/019; A61F 13/068; A61F 13/067; A61F 13/069; A61F 13/0246; A61F 13/102; A61F 5/0111; A61F 5/30; A61F 2013/00604; A61F 13/505; A61F 13/511; A61F 2013/0048; A61F 5/14; A61F 5/32; A61F 5/0195; A61F 5/34; A41B 11/00; A41B 2400/322; A41B 2500/10; A43B 7/142; A43B 7/144; A43B 7/14; A43B 7/141; A43B 13/12; A43B 7/1465; A43B 7/1435; A43B 7/145; A43B 7/1495; A43B 13/40; A43B 13/42; A43B 23/07; A43B 13/188; A43B 7/148; A43B 17/006; A43B 21/28; A43B 23/0265; A43B 13/386; A43B 3/108

See application file for complete search history.

(56) References Cited

U.S. PATENT DOCUMENTS

| | | | | |
|---|---|---|---|---|
| 4,524,529 A * | 6/1985 | Schaefer | ................ | A43B 13/38 36/98 |
| 4,658,515 A * | 4/1987 | Oatman | ................ | A43B 17/14 36/2.6 |
| 5,421,874 A * | 6/1995 | Pearce | ................ | A43B 5/0405 106/122 |
| 5,617,650 A * | 4/1997 | Grim | ................ | A43B 7/147 36/154 |
| 6,848,200 B1 * | 2/2005 | Westin | ................ | A43B 13/187 128/882 |
| 7,037,571 B2 * | 5/2006 | Fish | ................ | A43B 13/02 36/37 |
| 2018/0338573 A1 * | 11/2018 | Cross | ................ | A43B 13/04 |
| 2019/0330795 A1 * | 10/2019 | Schott | ................ | D04B 1/24 |

* cited by examiner

*Primary Examiner* — Ophelia A Hawthorne
(74) *Attorney, Agent, or Firm* — Daly, Crowley, Mofford & Durkee, LLP (57) ABSTRACT

Described is an article of footwear (e.g. a sock or shoe liner) or a therapeutic vessel which includes fabric having therapeutic spheres, or spherical-type dimensional objects, disposed therein. The therapeutic spheres are positioned in the fabric such that when the fabric is placed on (or otherwise placed in contact with) a foot, the variable positioning spheres, which may be of varied diameters, align with and contact desired compression areas on the sole of the foot.

17 Claims, 5 Drawing Sheets

THERAPEUTIC VESSEL, RELATED FOOTWEAR, AND METHOD OF MANUFACTURE AND USE

GOVERNMENT RIGHTS

Not applicable.

FIELD

The concepts, articles and techniques described herein relate to wearable clothing articles intended for the general reduction of stress on the bones, muscles, tendons, ligaments and soft tissue in the foot and to prevent and reduce pain relating to a variety of foot injuries and more particularly to therapeutic socks or sock linings.

BACKGROUND

The benefits of massage are well known as an effective treatment for reducing stress, anxiety, muscle tension and pain and increasing circulation, improving sleep, promoting general relaxation throughout the entire body, as well as many other benefits. Many places of the body are considered primary places to massage. One of such places that has been found to help people relax and reduce stress is the foot. People also find that foot massages reduce pain associated with a variety of foot injuries.

Plantar Fasciitis is a common form of foot and heel pain. Reportedly, plantar fasciitis is a clinical condition characterized by inflammation and thickening of the plantar fascia. This may be as a result of excessive stress applied to the plantar fascia, for example. The plantar fascia is made up of a thick fibrous band of connective tissue beneath the skin on the bottom of a foot that stretches outward from the heel bone, like a strong piece of elastic, and then spans out across the arch of the foot and through the ball area of the foot toward the base of the toes. The plantar fascia, along with several muscles in the foot, support the arch of the foot. This ligament is meant to support the bounce and spring of normal daily activity. However, in the case of plantar fasciitis, the plantar fascia is stretching and moving more than it should. Each time a person takes a step, the fibrous tissue stretches, and when it is stretched too hard and too often, the tissue becomes irritated and inflamed.

The inflammation of the plantar fascia results in the feeling of pain in the bottom of a foot. This type of inflammation is prevalent with runners, overweight people, people who have flat feet, high arches, or who spend a considerable amount of time on their feet. The pain is usually worse following activity. Stiffness can worsen after prolonged periods of time. Additionally, during this time of inflammation, calcium build-ups, called bone spurs, may form on the heel bone. These pointed bony protrusions press into the fatty pad of the heel with each step taken, causing further pain.

According to the American Academy of Orthopedic Surgeons, 1 out of 10 people struggle with Plantar Fasciitis sometime during their lifetime. Approximately one third of these people are affected in both feet.

These foot injuries can be caused and exacerbated by many things. One problem is the constant pounding caused by the hard, flat, surfaces upon which we walk. Long periods of standing or running also cause injuries, along with being overweight, having poorly fitting shoes, having tight Achilles tendons, and by having your feet rolling inwards as you walk.

Along with rest and wearing the correct shoes, stretching and caring for this muscle band is one way to ease foot pain and restore foot strength. Early diagnosis and treatment of any foot injury, including plantar fasciitis, is of major importance and can help patients to manage foot symptoms and reduce health and health related costs.

One such treatment is foot massage therapy, or in particular, sole massage therapy. Sole massage therapy stimulates certain areas of the skin and underlying tissues, and is used to relieve stress, anxiety, muscle tension and pain, as well as to heal particular physical conditions such as the pain caused by plantar fasciitis. Sole massage has been traditionally practiced by hand. However, such massage is quite tiring, and can be quite difficult for the practitioner, thereby limiting the availability of such treatment. Furthermore, the cost of receiving such a hand massage is quite expensive.

Published reports show conventional socks having elastomeric material having arch or heel supports. These provide relatively little effective therapeutic results, but they have the advantage of being adaptable to a wide range of foot sizes, and thus, they can be produced and sold inexpensively to a wide range of people.

Published reports also show compression socks which impart compression forces on the upper portion of the arch, these socks fail to protect or restore the sole of the foot, nor do they provide a therapeutic effect to the sole of the foot.

Published reports also show orthotic inserts, both custom fit and mass produced, both of which are formed of incompressible materials. These are very rigid, and provide a high degree of effective arch support, but because of their rigidity, must be custom fitted to the user's foot. Other inserts put tension on a wearer's plantar fascia as a result of their heel pounding on the ground with each step taken.

Published reports also show electric and manual massage devices that incorporate rollers on top of which, or within which, a foot is placed. The movement of the rollers in the electric devices or the movement of the foot in the manual devices provide for the release of tension in the sole of the foot. These devices, however, are large, heavy and cumbersome, and may require an accessible outlet to receive electricity.

It would, therefore, be desirable to provide an article of footwear (or more simply, an article which may, for example, be footwear such as a sock or shoe liner) which imparts a therapeutic effect on the sole of the foot and which may help a wearer obtain general stress and anxiety relief, increase circulation, promote general relaxation throughout the entire body as well as manage symptoms resultant from foot injuries, including plantar fasciitis and/or other issues.

SUMMARY

In accordance with the concepts, articles and techniques described herein an article of footwear (e.g. a sock or shoe liner) or a therapeutic vessel includes fabric having therapeutic spheres, or spherical-type dimensional objects, disposed therein. The therapeutic spheres are positioned in the fabric such that when the fabric is placed on (or otherwise placed in contact with) a foot, the variable positioning spheres, which may be of varied diameters, align with and contact desired compression areas on the sole of the foot.

With this particular arrangement, footwear (such as a sock or a shoe lining) or a therapeutic vessel, which exhibits soothing comfort, relaxation, and flexibility while also providing therapeutic healing effects on a person's foot is provided. With proper placement of the spheres, a person's longitudinal plantar arch and transverse plantar arch formed by the bones of the foot may be continuously soothed and massaged which may assist in proper healing of conditions of the lower extremities in general and which may assist in proper healing of certain foot conditions, in particular. Thus, the sock or other footwear or therapeutic vessel impart support, comfort, and healing of the bottom of a foot.

The footwear or therapeutic vessel described can also provide a therapeutic effect on the plantar fascia when a foot within the sock opposes the plantar fascia and is then simultaneously rolled over the object or objects (such as spheres) in the footwear. When a foot is within the sock, by repeatedly rolling the foot over the round objects or spheres also disposed within the sock, and applying increasing downwards pressure on the sole, the ligaments on the bottom of a foot, including the plantar fascia, is massaged, soothed and stretched. By disposing such spheres, either of the same or different diameters, in the article such that the spheres are arranged across the entire bottom of the foot (or substantially the entire bottom of the foot), the application of downward pressure on the sole can be utilized to massage from the heel to the toes of the foot, thereby stretching or acting upon muscles and ligaments on the bottom of the foot, as a well as increasing blood flow to all areas of the bottom of the foot.

The footwear described herein thus provides a structure which massages the sole of a foot through the use of downward pressure on the sole onto the spheres.

The footwear described herein massages the sole areas of the foot and thus provides general stress and anxiety relief and facilitates the treatment of at least some conditions such as plantar fasciitis and thus provides a form of a therapeutic experience.

The concepts, footwear and techniques described herein relate generally to a therapeutic massaging sock or foot lining device which enables the foot to relax, soothe and generally begin to heal and recover naturally. In embodiments, such footwear may take the form of a therapeutic sock or foot lining device in which a plurality of variable positioning spheres are securely contained in designated regions within the sock or foot lining device. The spheres are generally disposed as variable positioning spheres within a dimensionally expandable containment vessel of the sock or foot lining device enabling the rotation of the spheres to accommodate to the movement of the user's foot. In embodiments, such footwear may take the form of a therapeutic sock or foot lining device in which a plurality of variable positioning spheres are contained in designated regions of a containment vessel on a bottom of a sock or foot lining device such that, when the therapeutic sock or foot lining device is worn by a user, the spheres contact a bottom (or sole) portion of the user's foot.

The concepts described herein may include any of the following aspects in various combinations and may also include any other aspect described below in the written description or in the attached drawings. In one aspect, a sock comprises a first region having a plurality of variable positioning spheres, disposed within a first designated region of a containment vessel roughly encompassing a heel region of a user. The sock further comprises a second region having a plurality of variable positioning spheres, disposed within a second designated region of a containment vessel, roughly encompassing an arch region of a foot. The sock further comprises a third region having a plurality of variable positioning spheres, disposed within a third designated region of a containment vessel, roughly encompassing the metatarsal region, or ball of the foot, between the arch of the foot and the toes.

In another aspect, the sock or shoe lining also comprises a fourth region having a plurality of variable positioning spheres, disposed within a fourth designated region of a containment vessel, roughly encompassing the toes of the foot.

In yet another aspect of the concepts sought to be protected herein, the sock or shoe lining comprises a fifth region having a plurality of variable positioning spheres, disposed within a fifth designated region of a containment vessel, roughly encompassing the perimeter of the foot.

In another aspect, two or more of the designated regions of a containment vessel are continuous, without isolation, from each other. In yet another aspect, all the designated regions of the containment vessel may be continuous, without separation, thereby providing for a single designated region of the containment vessel on the surface of the sole of the foot.

In another aspect, the number, diameter and thickness of the spheres in each individual spherical designated regions may be the same. In another aspect, the number, diameter and thickness of the spheres in each individual spherical designated region may be different from the spheres in another spherical designated region. In yet another aspect, the spheres in the spherical designated regions may be of varying diameters and of varying thicknesses in the same spherical designated region.

BRIEF DESCRIPTION OF THE DRAWINGS

The concepts, footwear and techniques will be understood and appreciated more fully from the following detailed description taken in conjunction with the appended drawings in which.

DETAILED DESCRIPTION

Referring to the drawings and particularly to FIGS. 1 through 7, in which like elements are provided having like reference designations throughout the several views, footwear in the form of a therapeutic sock or shoe lining is shown. The term "sock" as used herein means a short, close fitting covering for the foot constructed in whole or in part from any suitable material including, but not limited to a flexible material, such as fabric. In one embodiment, the article comprises a sock construction 10 constructed from a flexible material, such as fabric. The fabric comprising the sock can be of various thicknesses as, for example, between about 0.0001 inches and about 2 inches. The term "fabric" as used herein means a sheet structure made from any suitable material including, but not limited to, natural fibers, synthetic fibers, closed cell foams, open cell foams, filaments, yarns or any combination thereof. Non-limiting examples include woven or non-woven sheets made by weaving, knitting, or felting. The fabric can be both machine washed and dried without losing its shape.

As shown in FIGS. 1, 2 and 3A-3F, an intermediate containment vessel 12 is affixed to sole portion 20 of sock 10, the sole portion 20 having an outer surface 30 in contact with a shoe or floor and an inner surface 32, affixed to the containment vessel 12. The material from which containment vessel 12 is provided has structural characteristics such that the containment vessel has the capability of generally conforming to the contours of the human foot so that it can be comfortably worn inside a boot or shoe as a sock lining or worn independently of a boot or shoe as a therapeutic vessel.

Figure 1:
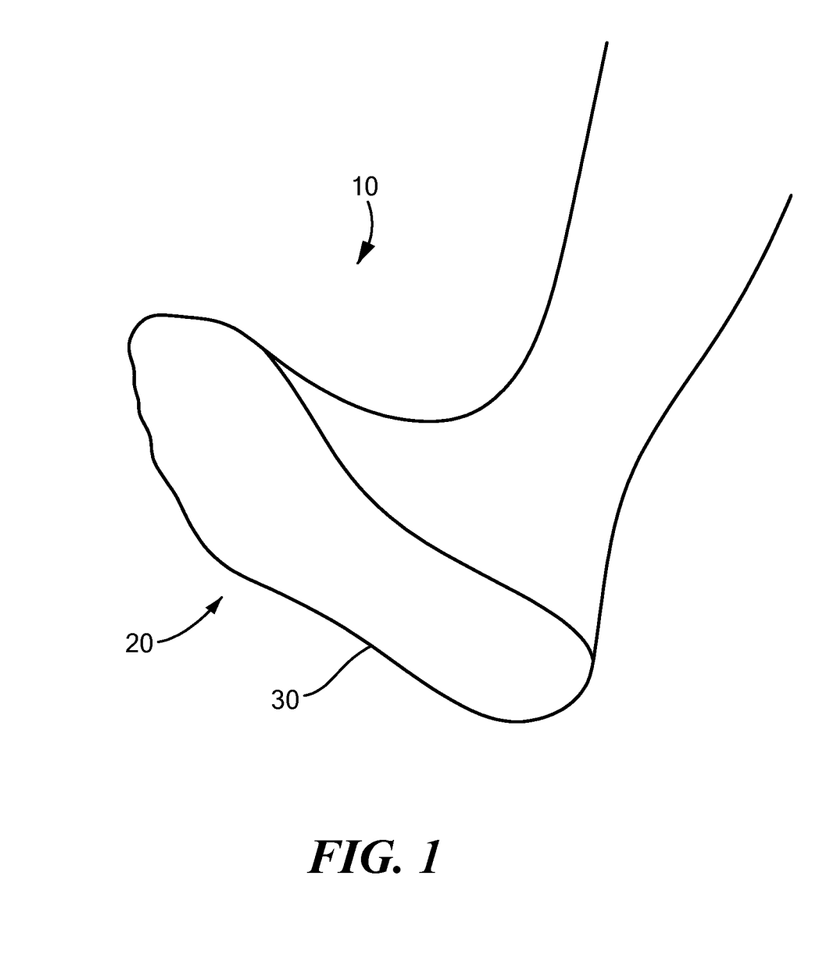
FIG. 1 is a side-elevational view illustrating the footwear and showing the components of the article in position.
Figure 2:
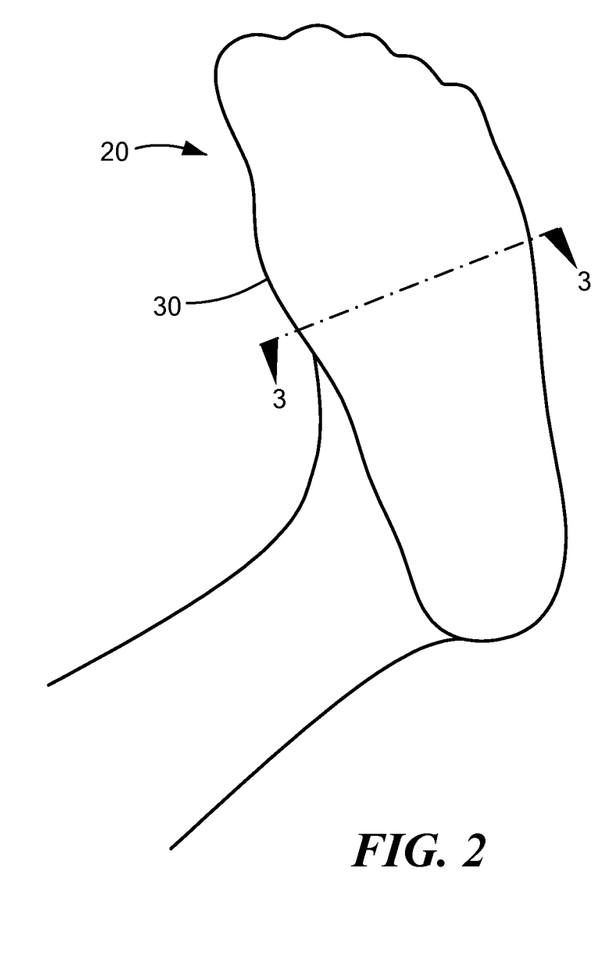
FIG. 2 is a bottom view showing the intended relation of the sock to a human foot.
Figure 3A:
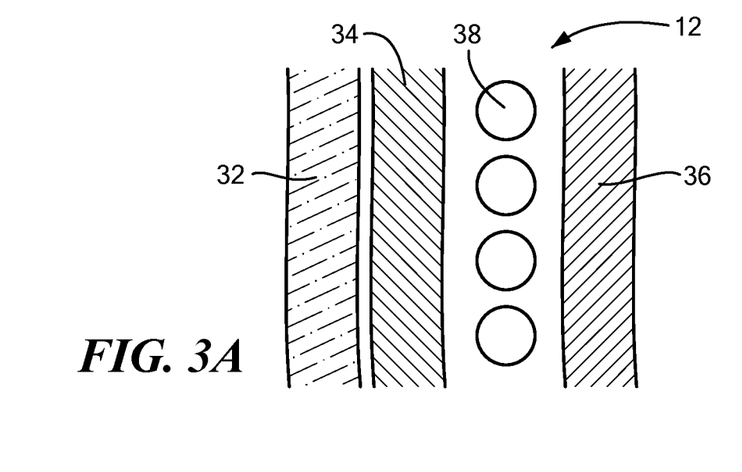
FIG. 3A is an enlarged, cross-sectional view showing one embodiment taken along line 3-3 of FIG. 2.
Figure 3B:
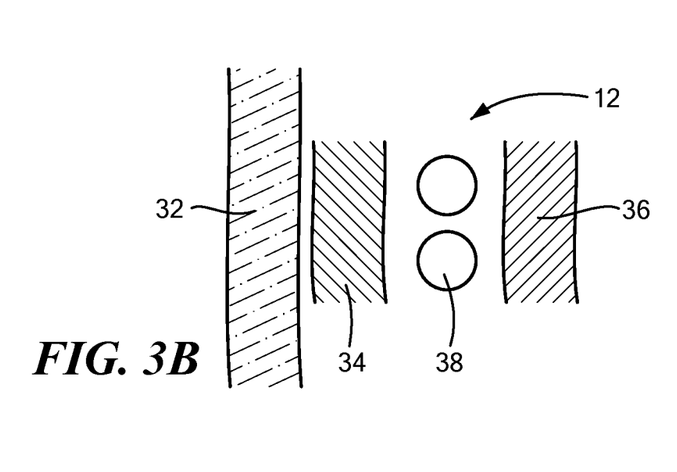
FIG. 3B is an enlarged, cross-sectional view showing another embodiment taken along line 3-3 of FIG. 2.

As shown in FIGS. 3A and 3B, containment vessel 12 may be affixed directly to the inner surface 32 of the of the sole portion 20. The article shown in FIGS. 3A and 3B also includes an inner containment vessel surface 34 and outer containment vessel surface 36, which is disposed proximate the inner surface 32 of sole portion 20.

Figure 3C:
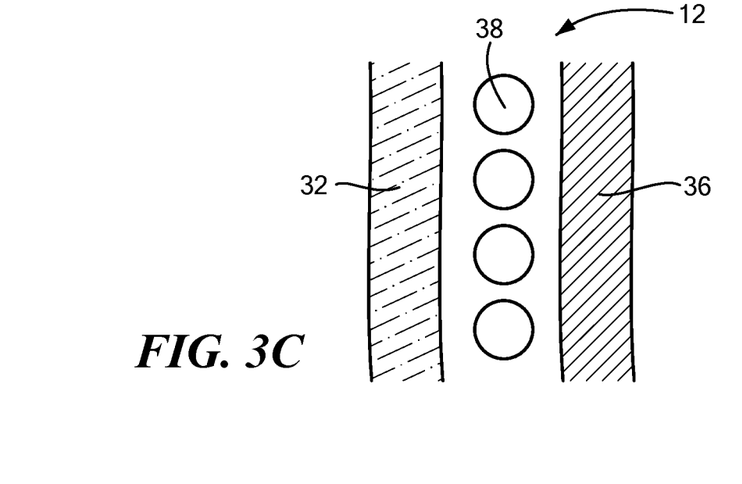
FIG. 3C is an enlarged, cross-sectional view showing another embodiment taken along line 3-3 of FIG. 2.
Figure 3D:
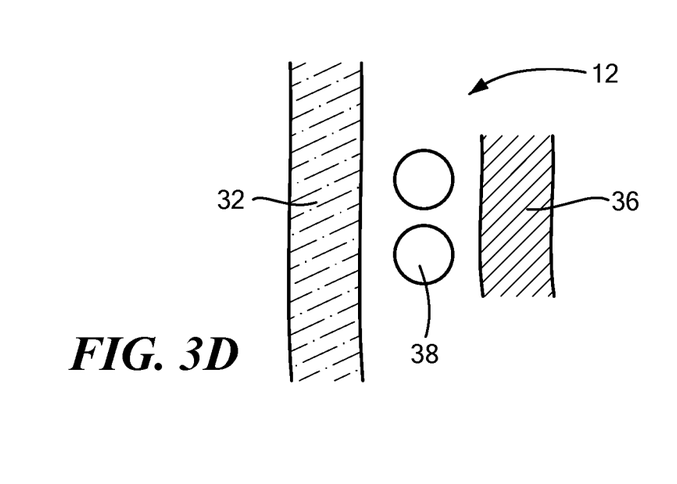
FIG. 3D is an enlarged, cross-sectional view showing another embodiment taken along line 3-3 of FIG. 2.

Alternatively, as shown in FIGS. 3C and 3D, containment vessel 12 is formed by affixing the inner surface 32 of sole portion 20 to an outer containment vessel surface 36, thereby eliminating the need for a separate inner containment vessel surface 34.

Figure 3E:
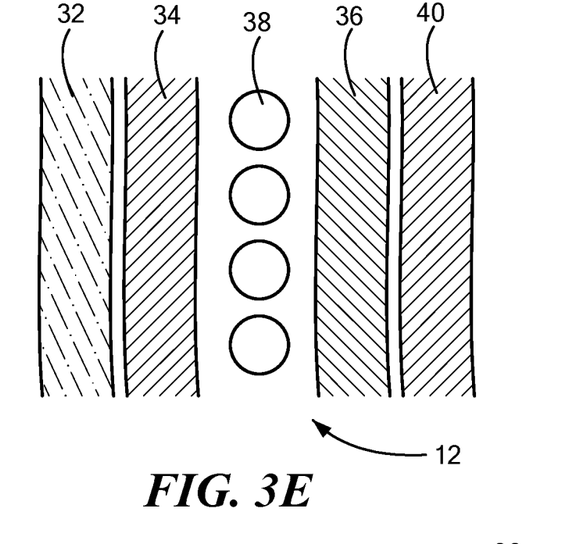
FIG. 3E is an enlarged, cross-sectional view showing another embodiment taken along line 3-3 of FIG. 2.
Figure 3F:
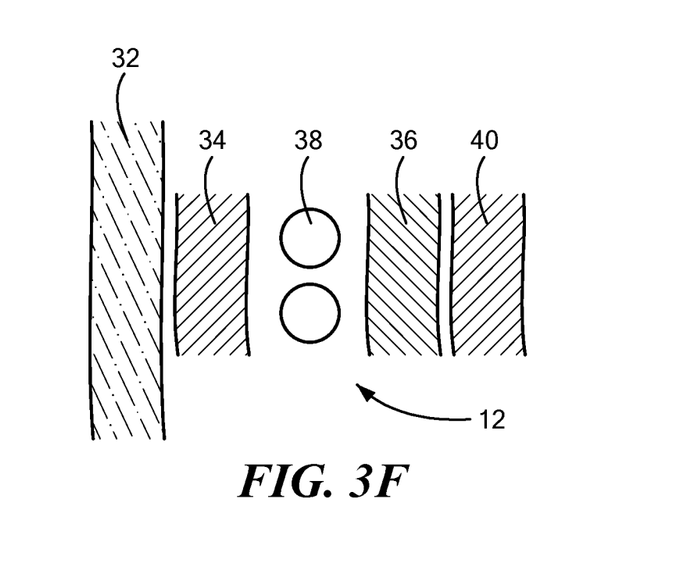
FIG. 3F is an enlarged, cross-sectional view showing another embodiment taken along line 3-3 of FIG. 2.

Alternatively, as shown in FIGS. 3E and 3F, containment vessel 12 may be affixed between inner surface 32 and covering member 40, thereby creating a more insulated, heavier portion which may provide a cushioning characteristic. The article shown in FIGS. 3E and 3F also includes containment vessel 12 comprised of an inner containment vessel surface 34 and outer containment vessel surface 36. Containment vessel 12 is disposed between and affixed to inner surface 32 of sole portion 20 of sock 10 and covering member 40.

Figure 3G:
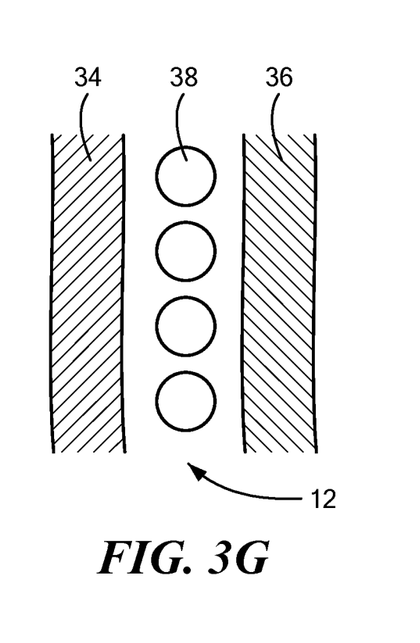
FIG. 3G is an enlarged, cross-sectional view showing one embodiment of the therapeutic vessel taken along line 3-3 of FIG. 2.

Alternatively, as shown in FIG. 3G, the containment vessel 12 may be utilized independently by a user as a therapeutic vessel without being affixed to a sock portion or used within a shoe or boot.

Affixing of such surfaces and members may consist of sewing, gluing or other permanent bonding methods. Such containment vessel 12 is preferably made from knitted natural or synthetic fibers.

Outer sock 10 can also be constructed from filament or spun yarns. The sock can also be constructed from natural fibers such as wool fibers, or from a variety of synthetic fibers such as polyester, nylon and combinations thereof.

Outer containment vessel surface 36 or alternatively covering member 40, may also have a coefficient of friction relative to the user's foot, thereby providing resistance to the sliding movement of the foot along the outer containment vessel surface 36 or covering member 40. Outer containment vessel 36 or covering member 40 are also constructed from knitted natural or synthetic fibers which will not pull or pinch during use and which provide ease of comfort for long-term use.

As best seen in FIGS. 3A and 3B, disposed between inner containment vessel surface 34 and outer containment vessel surface 36 on the bottom portion of the foot are a multiplicity of spherical-type dimensional objects, such as spheres, generally designated as 38. In this embodiment, the present invention teaches a method of making a custom article of footwear as shown in FIGS. 3A and 3B comprising the steps of providing a sole portion 20, affixing together an inner containment vessel surface 34 and outer containment vessel surface 36 to form a containment vessel 12 adapted to receive one or a plurality of spheres 38 into the containment vessel 12. The spheres 38 may be deposited into the containment vessel 12 by an insertion means such as an opening in the containment vessel 12, or any other means which would enable the depositing of the spheres 38. The spheres 38 may be deposited into the containment vessel 12 either before or after the containment vessel 12 is formed. If the spheres 38 are deposited prior to the formation of the containment vessel 12, the containment vessel 12 may be formed without the insertion means to deposit the spheres 38. In such method, the spheres 38 are deposited onto the inner containment vessel surface 34 and then the outer containment vessel surface 36 is affixed to the inner containment vessel surface 34 encapsulating the spheres 38 within. The containment vessel is further affixed together in one or more of a plurality of designated regions to isolate the spheres 38 into the designated regions. The containment vessel 12 may have a length substantially similar to the length of the sole portion 20, as shown in FIG. 3A, or it may be shorter, as shown in FIG. 3B. The containment vessel 12 is then affixed to the inner surface 32 of the sole portion 20. In such embodiment, the containment vessel 12 may be removed from the sock 10, and if desired, may be used as a separate independent lining.

Alternatively, as shown in FIGS. 3C and 3D, spheres 38 may be disposed between the inner surface 32 of sole portion 20 of sock 10 and the outer containment vessel surface 36. In such embodiment, the containment vessel 12 is formed directly with the inner surface 32 of sole portion 20 of sock 10 and the outer containment vessel surface 36 and is not independently removable from the sock 10. In this embodiment, the present invention teaches a method of making a custom article of footwear as shown in FIGS. 3C and 3D comprising the steps of affixing together a sole portion 20 and an outer containment vessel surface 36 to form a containment vessel 12 adapted to receive one or a plurality of spheres 38 into the containment vessel 12. The spheres 38 may be deposited into the containment vessel 12 by an insertion means such as an opening in the containment vessel 12, or any other means which would enable the depositing of the spheres 38. Similar to the method described above, the spheres 38 may be deposited into the containment vessel 12 either before or after the containment vessel 12 is formed. If the spheres are deposited prior to the formation of the containment vessel 12, the containment vessel 12 may be formed without the insertion means to deposit the spheres 38. In such method, the spheres 38 are deposited onto the inner surface 32 of the sole portion 20 and then the outer containment vessel surface 36 is affixed to the inner surface 32 encapsulating the spheres 38 within. The containment vessel 12 is further affixed together in one or more of a plurality of designated regions to isolate the spheres 38 into the designated regions. The containment vessel 12 may have a length substantially similar to the length of the sole portion 20, as shown in FIG. 3C, or it may be shorter, as shown in FIG. 3D.

Alternatively, as shown in FIGS. 3E and 3F, the spheres 38 may be disposed between inner containment vessel surface 34 and outer containment vessel surface 36, which forms containment vessel 12. Such containment vessel 12 is disposed between inner surface 32 of sole portion 20 of sock 10 and covering member 40. Such containment vessel 12 may be removed from the sock 10, and if desired, may be used as a separate independent lining, similar to the containment vessel shown in FIGS. 3A and 3B above. In this embodiment, the present invention teaches a method of making a custom article of footwear as shown in FIGS. 3E and 3F comprising the steps of providing a sole portion 20, affixing together an inner containment vessel surface 34 and outer containment vessel surface 36 to form a containment vessel 12 adapted to receive one or a plurality of spheres 38 into the containment vessel 12. The spheres 38 may be deposited into the containment vessel 12 by an insertion means such as an opening in the containment vessel 12, or any other means which would enable the depositing of the spheres 38. The spheres 38 may be deposited into the containment vessel 12 either before or after the containment vessel 12 is formed. If the spheres 38 are deposited prior to the formation of the containment vessel 12, the containment vessel 12 may be formed without the insertion means to deposit the spheres 38. In such method, the spheres 38 are deposited onto the inner containment vessel surface 34 and then the outer containment vessel surface 36 is affixed to the inner containment vessel surface 34 encapsulating the spheres 38 within. The containment vessel is further affixed together in one or more of a plurality of designated regions to isolate the spheres 38 into the designated regions. The containment vessel 12 may have a length substantially similar to the length of the sole portion 20, as shown in FIG. 3E, or it may be shorter, as shown in FIG. 3F. The containment vessel 12 is then affixed between an inner surface 32 of the sole portion 20 and a covering member 40. The covering member may have a length substantially similar to the length of the sole portion 20, as shown in FIG. 3E, or it may be shorter, as shown in FIG. 3F.

Alternatively, as shown in FIG. 3G, the spheres 38 may be disposed between inner containment vessel surface 34 and outer containment vessel surface 36, which forms containment vessel 12 adapted to receive one or a plurality of spheres 38 into the containment vessel 12. The spheres 38 may be deposited into the containment vessel 12 by an insertion means such as an opening in the containment vessel 12, or any other means which would enable the depositing of the spheres 38. The spheres 38 may be deposited into the containment vessel 12 either before or after the containment vessel 12 is formed. If the spheres 38 are deposited prior to the formation of the containment vessel 12, the containment vessel 12 may be formed without the insertion means to deposit the spheres 38. In such method, the spheres 38 are deposited onto the inner containment vessel surface 34 and then the outer containment vessel surface 36 is affixed to the inner containment vessel surface 34 encapsulating the spheres 38 within. The containment vessel 12 may be utilized independently by a user as a therapeutic vessel without being affixed to a sock portion or used within a shoe or boot.

Alternatively, in each of the embodiments shown in FIGS. 3A-3G, the spheres 38 may be deposited into the containment vessel 12 by the user of the therapeutic footwear to enable the user to independently determine the desired amount and size of the spheres 38. In such embodiment, the user may deposit the spheres 38 by the insertion means of the containment vessel 12. In such embodiment, the user may also independently affix the containment vessel 12 to encapsulate the spheres within. In such embodiment, the user may also determine the desired amount and location of designated regions within which to isolate the spheres 38 by the user affixing the designated regions of the containment vessel 12.

Spheres 38 are generally commercially available and can vary in diameter from between about 0.015625 inches and about 4 inches. Spheres 38 may be textured, e.g., dimpled like a golf ball. Spheres 38 may also be generally spherical but may be provided with a plurality of flat sides thereby being capable of movement. Spheres 38 may also be octagonally shaped or elongated into a generally oval shape, such as a football. The spheres 38 are constructed and arranged such that when brought into contact with the bottom of a user's foot, the spheres function so as to substantially stimulate blood flow in one or more regions of a bottom portion of a foot and relax the muscles and ligaments, as well as help the tissues, such as the plantar fasciitis, heal. The spheres also serve to soothe generally tired feet and provide a pleasure-seeking experience while removing any pain. The spheres 38 are generally disposed as variable positioning spheres within the containment vessel 12, enabling the rotation of the spheres to accommodate to the movement of the user's foot.

More particularly, each variable positioning sphere 38 may have a latitude of excursion, which may consist of a rotation, or other movement or traversal of distance, within the containment vessel 12. Each containment vessel 12 accommodates such excursion of the spheres by having a length which is at least the length of 0.0156 of the circumference of the largest sphere 38 within the containment vessel, or 0.0156 of the shortest circumference of the sphere 38, in the event the sphere 38 is not of a spherical shape. Accordingly, each containment vessel 12 is enabled to accommodate at least a portion of one rotation of the spheres disposed within.

Further, the flexure or stretchability of the knitted, natural or synthetic fibers of the containment vessel 12 enables the dimensional expandability of the containment vessel. Such dimensional expandability enables the excursion of the spheres within the containment vessel. Such excursion of the spheres is enabled by the flexure or stretchability of the fibers of the containment vessel 12 such that spheres may be affixed to such containment vessel, such as by means of bonding, or gluing, and remain capable of such excursion and variable positioning.

Figures 4, 5:
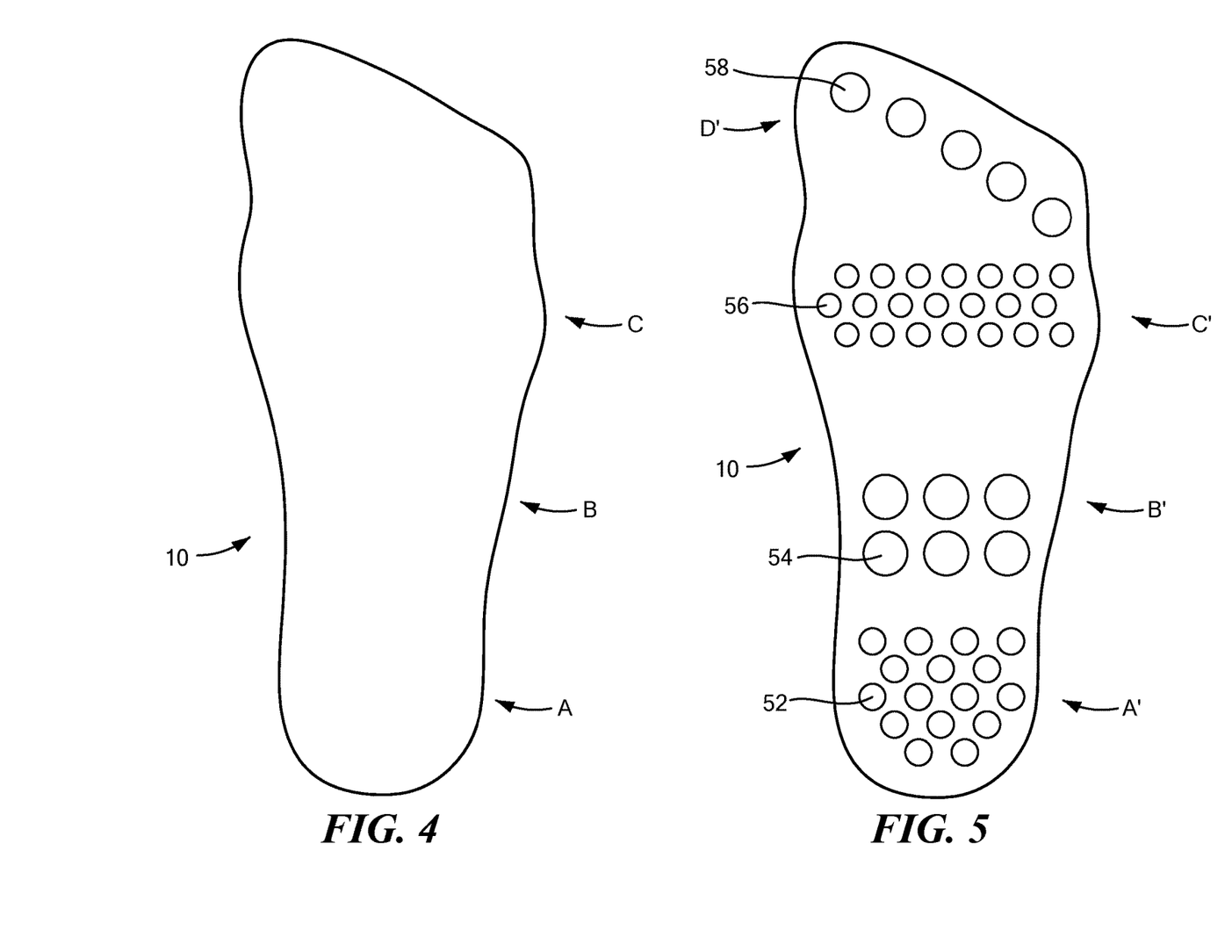
FIG. 4 is a bottom elevational view of one form of the footwear.
FIG. 5 is a bottom elevational view showing one embodiment of the plurality of spheres contained in designated regions on the bottom of the foot.

As shown in FIG. 4, in embodiments, the sock 10 is intended to be worn with the heel region A located beneath the user's heel, the arch region B locating beneath the user's arch and the metatarsal region C locating proximally of the heads of the user's metatarsal joints on the ball of the foot.

As shown in FIG. 5, the sock 10 comprises a first region A' having one or a plurality of variable positioning spheres 52, disposed within the containment vessel in a designated region, roughly encompassing at least a portion of (and in some cases substantially all of) the heel region A'. The sock 10 further comprises a second region B' having one or a plurality of variable positioning spheres 54, disposed within the containment vessel in a designated region, roughly encompassing at least a portion of (and in some cases substantially all of) the arch region B'. The sock further comprises a third region C' having one or a plurality of variable positioning spheres 56, disposed within the containment vessel in a designated region, roughly encompassing at least a portion of (and in some cases substantially all of) the metatarsal region, or ball of the foot, between the arch of the foot and the toes.

Figure 6:
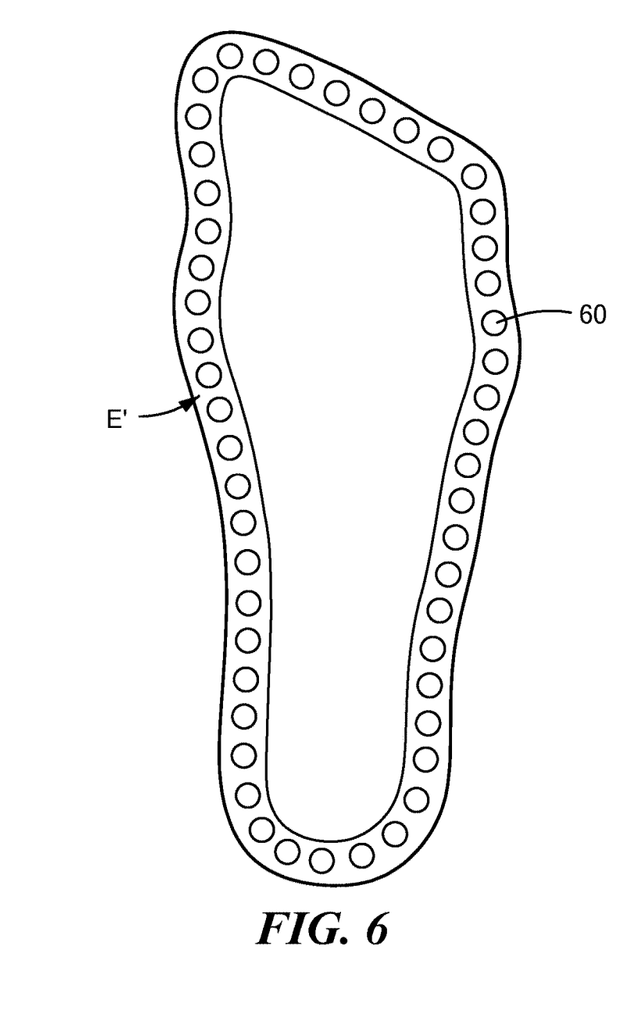
FIG. 6 is a bottom elevational view showing another embodiment of the plurality of spheres contained in designated regions on the bottom of the foot.

In embodiments, the sock or shoe lining also comprises a fourth region D', shown in FIG. 5, having one or a plurality of variable positioning spheres 58, disposed within the containment vessel in a designated region, roughly encompassing at least a portion of (and in some cases substantially all of) the toes of the foot. It is noted that to avoid discomfort in the toe region while wearing the sock, the inside part of the sock in the toe region is stretched and subjected to a reactive force from the inner surface of the toe portion of the sock subsequent to the insertion of the spheres. In yet another embodiment, as shown in FIG. 6 for example, the sock or shoe lining comprises a fifth region E' having one or a plurality of variable positioning spheres 60, disposed within the containment vessel in a designated region, roughly encompassing at least a portion of (and in some cases substantially all of) the perimeter of the foot.

By the placement of the spheres, the bottom of the foot (and ideally all areas of the bottom of a foot), including the plantar fascia, can be exercised. Such exercising takes place when a foot within the sock or the therapeutic vessel opposes the plantar fascia and the foot is rolled over the spheres in the sock or the therapeutic vessel and increased downward pressure is applied on the sole. This may be accomplished with or without the addition of a shoe. By repeated rolling of the variable positioning spheres, and by applying such increasing downwards pressure on certain regions of the sole, as chosen by the user of the footwear, the ligaments on the bottom of a foot (and ideally all ligaments on the bottom of a foot) are massaged, soothed and exercised. Further, such massage in some embodiments provides the added benefit of increasing blood flow to chosen areas of the bottom of the foot (and ideally to all areas of the bottom of the foot). Still further, by applying direct pressure and relief to all the possibly affected areas of the ligament, the plantar fascia ligament, if desired, may be pushed back into its natural position.

This beneficial massage by the spheres is created not only as the user takes each step, but also, when the user is at rest. At such time, the user may apply increasing downward pressure on the sole onto the spheres, thereby creating a massaging effect to the bottom of the foot. Furthermore, a user not experiencing any foot pain may also desire to wear the footwear or the therapeutic vessel to generally soothe tired feet as well as to experience the pleasure of a massage on the bottom of the foot for enhanced relaxation, comfort and health. A user may choose to use the footwear described herein within their shoe to experience the beneficial massage while taking each step while walking or to use the footwear or the therapeutic vessel only while at rest with or without the addition of a shoe. Either of such uses enable the user to maximize the benefit from the massage of the spheres while they are at home, in transit, at work, or any other desired location.

It is understood that in embodiments, the spherical objects used in the footwear described herein may be commercially available, with walls made of elastomer, metal, glass, carbon, plastic or other similar materials. The interiors of the spheres may be filled or hollow or could have a gaseous, solid or liquid interior. The spheres may be comprised of compressible material, such as elastomer, foam, or fluid, thereby enabling the user to compress the spheres with each downward motion. In another embodiment, the spheres may be comprised of marbles, ball bearings, rubber balls, or any spherical shaped structure having varying hardness, densities and weights. The hardness of the spheres will allow a user to determine how much deep therapeutic pressure they desire on the bottom of the foot when they apply the downward pressure on the sole onto the spheres. Such decisions often will be determined by the degree or existence of chronic pain on the bottom of their foot.

In embodiments, the spheres may have a thickness of between about 0.001 inches to about 3 inches. The thickness also will be determined by the therapeutic effect desired by the user.

Similarly, in embodiments, the number of spheres displaced in a single region will vary depending on the size and thickness of the spheres. For example, in one embodiment, a single large sphere may be desired in only a single designated region of the sock. The number of spheres also will be determined by the therapeutic effect desired by the user.

It is understood that the spheres are disposed in a tightly packed substantially side by side relationship to each other such that the centers of the spheres in each containment vessel remain in the same plane while the spheres are at rest or while they have an excursion by the movement of the user's foot, thereby preventing the spheres from being displaced on top of one another while maintaining them in a sufficient closely packed manner. This placement of the spheres in the containment vessel prevents the unintentional movement by the user's foot while walking as well as the insertion of any of the toes into the spaces between the respective spheres.

In yet a further embodiment, the designated regions in which the spheres are located also include a lubricant to facilitate the excursion, such as the sliding and rolling movement, of the spheres. Such lubricant is applied to substantially coat the exterior surface of the spheres. The lubricant used may be any lubricant selected from the group consisting of oils, greases, silicone-based lubricants, vegetable-based lubricants, petroleum-based lubricants, mineral-based lubricants, water-based lubricants, synthetic lubricants, or any other friction reducing substance which permits the spheres to readily slide and roll in contact with each other.

In view of the tightly packed side by side relationship in which the spheres are disposed within the containment vessels, the lubrication would not cause the spheres to be displaced out of their position. Such lubrication, coupled with the plurality of spheres, will also provide a cushioning characteristic.

In embodiments, the sock or shoe lining or therapeutic vessel may be placed within a freezer for extended periods of time. This freezing of the sock or shoe lining or therapeutic vessel, and in particular, the freezing of the spheres would serve as cold therapy to the bottom of the foot, thereby aiding the elimination of the pain and inflammation. It is understood that in the event lubricant were utilized with the spheres, such lubricant would not have properties that would cause it to freeze when placed in a freezer. Rather, the frozen spheres displaced within the lubricant would remain free to slide and roll. Such mixture of spheres and lubricant may be contained in fluid-tight confinement within the containment vessel or sock portion.

In embodiments, the sock or shoe lining or therapeutic vessel may be placed within a microwave. This heating or warming of the sock or shoe lining or therapeutic vessel, and in particular, the heating or warming of the spheres would serve as heat therapy to transfer the heat to the bottom of the foot, thereby aiding the elimination of the pain and inflammation. It is understood that in the event lubricant were utilized with the spheres, neither the lubricant nor the spheres would have properties that would cause them to burn or melt when placed in the microwave. Rather, the heated spheres displaced within the lubricant would maintain their ability to move, slide, or roll. Such mixture of spheres and lubricant may be contained in fluid-tight confinement within the containment vessel or sock portion. Further the sock may be made from materials which would not irritate the user's foot or produce any undesired smells.

Figure 7:
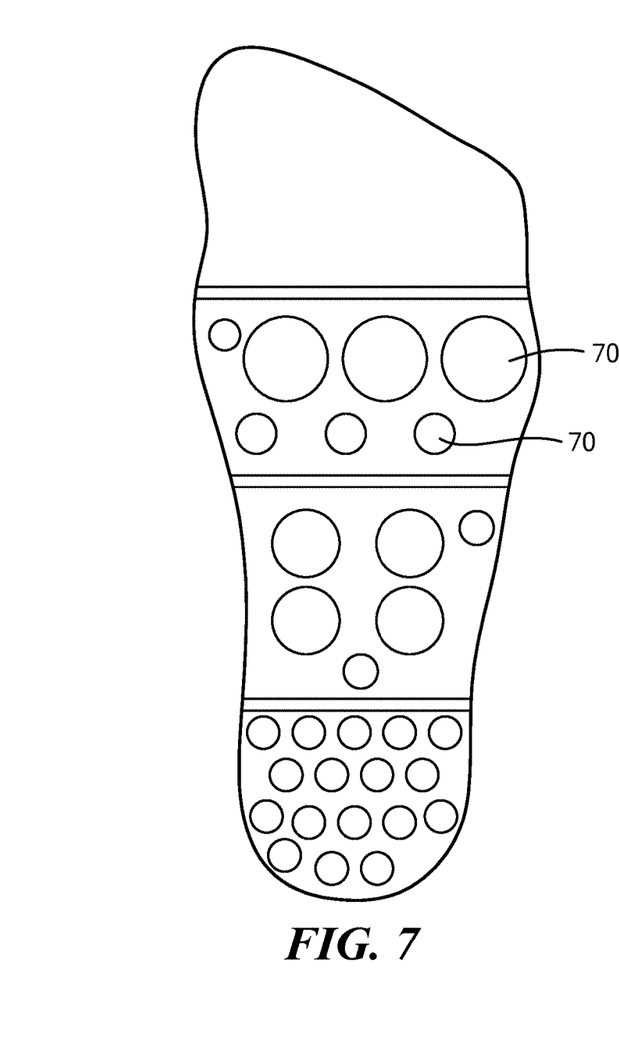
FIG. 7 is a bottom elevational view showing yet another embodiment of the plurality of spheres contained in designated regions on the bottom of the foot.

In an embodiment of the concepts sought to be protected and as shown in FIGS. 6 and 7, the spheres disposed within each designated region of the containment vessel are isolated, contained, sealed, and in non-communicative nature from the spheres disposed in adjacent designated regions of the containment vessel. This would provide for the spheres to remain in variable positioning close contact while avoiding any shifting when in use. Such isolation within each designated region of the containment vessel may also provide for the fluid tight confinement, which may be created by sewing, gluing, adhering, or otherwise bonding portions of the outer surface of containment vessel 12 and the inner surface of containment vessel 12. Alternatively, such isolation may be created by the bonding of portions of the upper portion of sock 10 and the inner surface 34 of containment vessel 12. Alternatively, boundaries between the designated regions of the containment vessel 12 may be removed to have a comingling of the spheres within the containment vessel 12, whether they are of the same or different sizes, in one or more of the designated regions. Alternatively, the spheres may be limitedly adhered to the lining such that the variable positioning nature of the spheres is minimized or prevented.

In another embodiment of the concepts sought to be protected, the size of the spheres within all of the designated regions are the same and the number of the spheres within all of the designated regions are the same. Alternatively, as shown in FIG. 5, each designated region could contain spheres of the same size, which differ from the sphere size in other designated regions of the same containment vessel. Alternatively, as shown in FIG. 7, each designated region could contain spheres 70 of different sizes. Alternatively, as shown in FIG. 5, the number of spheres within each designated region could differ from the number of spheres in the other designated regions. In yet another embodiment, as shown in FIG. 7 for example, one or more of the designated regions may contain spheres 70 while other designated regions may have no spheres at all.

In another aspect of the concepts sought to be protected, any two of the designated regions of the containment vessel may be continuous, without separation, from each other. In yet another aspect, all the designated regions of the containment vessel may be continuous, without separation.

In another aspect, the number, diameter and thickness of the spheres in each designated region may be the same. In another aspect, the number, diameter and thickness of the spheres in each designated region may be different from the spheres in another designated region. In yet another aspect, the spheres in the designated regions may be of varying diameters and of varying thicknesses in the same designated region.

In the footwear described herein, there may not be any particular limitations on the structure of components and a variety of embodiments may be employed, depending on the manufacturer's concept of the product, and depending on the preferences of the consumer.

While the disclosed concepts, articles and technique have been described and illustrated in conjunction with a number of specific embodiments, those skilled in the art will appreciate that variations and modifications may be made without departing from the principles of the concepts sought to be protected herein as herein illustrated, described and claimed. The concepts may be embodied in other specific forms without departing from its spirit or essential characteristics of the concepts sought to be protected. The described embodiments are to be considered in all respects as only illustrative, and not restrictive. The scope of the subject matter sought to be protected is, therefore, indicated by the appended claims, rather than by the foregoing description. All changes which come within the meaning and range of equivalency of the claims are to be embraced within their scope.

Having thus described the concepts, what is claimed is:

1. An article of footwear comprising:
   a. a sole portion of the article of footwear, the sole portion conformable to a sole of a user's foot;
   b. an inner containment vessel surface coupled to an outer containment vessel surface to form a containment vessel;
   c. the containment vessel having one or more regions;
   d. a plurality of spheres contained within each of said one or more regions of said containment vessel, wherein the plurality of spheres are disposed in a non-contacting relationship in each of said one or more regions and move independently from one another within the one or more regions when pressure is applied by the user's foot; and
   e. wherein the inner containment vessel surface and outer containment vessel surface are removable from the inner surface of the sole portion of the article of footwear and a covering member such that the containment vessel is removable from the inner surface of the sole portion of the article of footwear and the covering member.

2. The article of footwear as defined in claim 1, wherein said one or more regions corresponds to a plurality of regions in the containment vessel and wherein the plurality of regions includes a region configured to be aligned with a heel region, another region configured to be aligned with an arch region, and another region configured to be aligned with a metatarsal region in response to the footwear being disposed on a human foot.

3. The article of footwear as defined in claim 2, wherein the plurality of regions includes a region configured to be aligned, with a toe region in response to the footwear being disposed on a human foot.

4. The article of footwear as defined in claim 2, wherein said one or more regions includes a region configured to roughly encompass a perimeter of the foot.

5. The article of footwear as defined in claim 1 in which the containment vessel is disposed between said upper portion and a lower portion.

6. The article of footwear as defined in claim 1 in which the spheres are frozen.

7. The article of footwear as defined in claim 1 in which the spheres are heated.

8. The article of footwear as defined in claim 1 further comprising a lubricant disposed in the containment vessel.

9. The article of footwear as defined in claim 1 in which the spheres in each of said one or more regions are a same size.

10. The article of footwear as defined in claim 1 in which the spheres in each of said one or more regions are different sizes.

11. The article of footwear as defined in claim 1, wherein said one or more regions corresponds to a plurality of regions and wherein the plurality of regions are spaced from one another.

12. The article of footwear as defined in claim 1 in which the spheres in a single one of said one or more regions are a same size.

13. The article of footwear as defined in claim 1 in which the spheres in a single one of said one or more regions are different sizes.

14. The article of footwear as defined in claim 1, wherein said one or more regions corresponds to a plurality of regions, and wherein a same number of spheres are included in each of the plurality of regions.

15. The article of footwear as defined in claim 1, wherein said one or more regions corresponds to a plurality of regions, and wherein a different number of spheres are included in each of the plurality of regions.

16. The article of footwear as defined in claim 1 in which the spheres in each of said one or more regions have a same thickness.

17. An article of footwear comprising:
   a. inner surface of a sole portion of the article of footwear, the inner surface conformable to a sole of a user's foot;
   b. a covering member;
   c. an inner containment vessel surface and an outer containment vessel surface configured to form a containment vessel with the inner containment vessel surface and outer containment vessel surface disposed between the inner surface of the sole and the covering member;
   d. the containment vessel having one or more regions; and
   e. a plurality of spheres contained within each of said one or more regions of said containment vessel, wherein the plurality of spheres are disposed in a non-overlapping relationship in each of said one or more regions and maintain a variable positioning within said one or more regions; and
   f. wherein the inner containment vessel surface and the outer containment vessel surface are removable such that the containment vessel is removable from the inner surface of the sole portion of the footwear and the covering member.

\* \* \* \* \*